(12) United States Patent
Heeney et al.

(10) Patent No.: US 7,714,098 B2
(45) Date of Patent: *May 11, 2010

(54) MONO-, OLIGO- AND POLYTHIENO[3,2-B]THIOPHENES

(75) Inventors: Martin Heeney, Southampton (GB); Robert Wagner, Diebrug (DE); Iain McCulloch, Southampton (GB); Steven Tierney, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 578 days.

This patent is subject to a terminal disclaimer.

(21) Appl. No.: 11/596,850

(22) PCT Filed: Apr. 21, 2005

(86) PCT No.: PCT/EP2005/004271

§ 371 (c)(1), (2), (4) Date: Nov. 17, 2006

(87) PCT Pub. No.: WO2005/111045

PCT Pub. Date: Nov. 24, 2005

(65) Prior Publication Data

US 2007/0232812 A1    Oct. 4, 2007

(30) Foreign Application Priority Data

May 18, 2004 (EP) .................................. 04011713

(51) Int. Cl.
   *C08G 75/00* (2006.01)
(52) U.S. Cl. ..................................................... 528/377
(58) Field of Classification Search .................. 528/377
   See application file for complete search history.

(56) References Cited

U.S. PATENT DOCUMENTS

| | | | |
|---|---|---|---|
| 6,403,809 B1 * | 6/2002 | Holmes et al. | 549/41 |
| 2003/0080322 A1 * | 5/2003 | Farrand et al. | 252/299.62 |

FOREIGN PATENT DOCUMENTS

| | | |
|---|---|---|
| EP | 1275650 A1 | 1/2003 |
| EP | 1300430 A1 | 4/2003 |
| EP | 1327646 A1 | 7/2003 |
| EP | 1327647 A1 | 7/2003 |
| EP | 1329474 A1 | 7/2003 |
| EP | 1329475 A1 | 7/2003 |
| EP | 1510535 A1 | 3/2005 |
| WO | WO 99/12989 | 3/1999 |

OTHER PUBLICATIONS

Lance S. Fuller et al., "Thienothiophenes. Part 2. Synthesis, metallation and bromine—lithium exchange reactions of thieno[3,2-b]thiophene and its polybromo derivatives," J. Chem. Soc., Perkin Trans. 1, 1997, pp. 3465-3470.
Keun Soo Choi et al., "A One-Pot Synthesis of Substituted Thieno[3,2-b]thiophenes and Selenolo[3,2-b]selenophenes," Hetrocycles, 1994, vol. 38, No. 1, pp. 143-149.
S.B. Saidman et al., "Kinetic Study of 3,6-dimethylthieno[3,2-b]thiophene electropolymerisation," Journal of Applied Electrochemistry, 2001, vol. 31, pp. 839-844.
Juzo Nakayama et al., 'Synthesis and Characterization of Dimers, Trimers, and Tetramers of 3,6-Dimethylthieno[3,2-b]thiophene and 3,6-Dimethylselenolo[3,2-b]selenophene, Tetrahdron, 1996, vol. 52, No. 2, pp. 471-488.
Gerhard Koβmehl et al., "Uber Polyarylenalkenylene und Polyheteroarylenalkenylene, 12," Makromol. Chem.; 1982, vol. 183, pp. 2747-2769.
Denise R. Rutherford et al, "Poly(2,5-ethynylenethiophenediylethynyienes), Related Heteroaromatic Analogues and Poly(thieno[3,2-b]thiophenes). Synthesis and Thermal and Electrical Properties," Macromolecules, 1992, vol. 25, pp. 2294-2306.
Beng S. Ong et al., "High-Performance Semiconducting Polythiophenes for Organic Thin-Film Transistors," J. Am. Chem. Soc., American Chemical Society, 2003.
Search for Thieno[3,2-b]-Thiophene-Polymers. Scientific Information: Chemistry Medicine Buisness, Oct. 21, 2003.

* cited by examiner

*Primary Examiner*—Randy Gulakowski
*Assistant Examiner*—Shane Fang
(74) *Attorney, Agent, or Firm*—Millen, White, Zelano, Branigan, P.C.

(57) ABSTRACT

The invention relates to novel mono-, oligo- and polythieno [3,2-b]thiophenes, to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to field effect transistors, light emitting devices or ID tags comprising the novel polymers.

29 Claims, No Drawings

MONO-, OLIGO- AND POLYTHIENO[3,2-B]THIOPHENES

FIELD OF INVENTION

The invention relates to novel mono-, oligo- and polythieno[3,2-b]thiophenes. The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the novel polymers.

BACKGROUND AND PRIOR ART

In prior art polymers consisting of repeating thiophene units have been reported to show good performance as charge transporting materials in FET applications. For example, regioregular poly(3-alkyl)thiophene for example has demonstrated one of the highest recorded mobilities to date for a polymer (Sirringhaus et al., Science, 1998, 280, p 1741). Also, polythiophene analogues as disclosed for example in EP 1 327 646 A1, EP 1 327 647 A1, EP 1 329 474 A1 or EP 1 329 475 A1 containing different numbers and regioisomers of alkyl-thiophenes exhibit reasonable charge carrier mobilities.

This performance is thought to be due to two factors. Firstly the arrangement of the alkyl side-chains on the polymer backbone allows the polymers to self-organise into well-ordered structures on coating from solution. This facilitates the hopping mechanisms that dominate charge transport. Secondly the presence of sulfur atoms in the polymer backbone has been shown to be beneficial to charge transport. The exact mechanism is not known, but it is speculated that interaction of the sulfur d-orbitals on adjacent polymer chains facilitates the charge hopping mechanism.

However, the polymers disclosed in the above prior art documents do only show charge carrier mobilities of not more than 0.1 $cm^2V^{-1}s^{-1}$. Also, the materials of prior art often show only limited solubility which is a disadvantage when processing the polymers for the manufacture of semiconductor devices like thin film transistors (TFT) or field effect transistors (FET).

Therefore, further enhancement of the charge mobility and solubility of organic polymers is desired in order to enable transistor performance.

It is an aim of the present invention to provide new organic materials for use as semiconductors or charge transport materials, which are easy to synthesise, have high charge mobility and good processability. Especially the materials should be easily processible to form thin and large-area films for use in semiconductor devices. Also, the materials should be oxidatively stable, but retain or even improve the desired electrical properties.

The inventors of the present invention have found that materials based on thieno[3,2-b]thiophene (1) (TT)

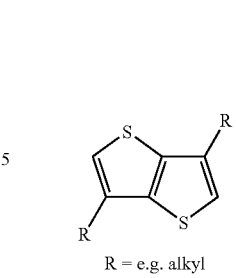

R = e.g. alkyl in particular oligomers and (co)polymers of TT comprising 3,6-disubstituted TT groups and/or substituted thiophene or selenophene groups, show improved charge carrier mobility whilst maintaining desirable solution processable properties.

TT materials are known in prior art. For example, Nakayama et al., Heterocycles 1994, 38, p. 143 report 3,6-dimethyl TT. Saidman et al., J. Appl. Electrochemistry, 2001, 31, p 839 report the electropolymerisation of 3,6-dimethyl TT which, however, only gives an insoluble polymer. Nakayama et al., Tetrahedron 1996, 52, p. 471 report dimers, trimers and tetramers of 3,6-dimethyl TT. Again the tetramers are of very low solubility and no electrical properties are reported.

Fuller et al., J. Chem. Soc. Perkin Trans. 1997, 1, 3465-70 report 3,6-disubstituted TT with thioalkyl (—S-Me, —S-Ph) and silylalkyl (—Si(Me)$_3$) substituents. However, polymers are not disclosed. Also, thioethers are often undesired because the electron rich nature of these side chains affords polymers that are oxidatively unstable.

In prior art there are also some reports of polymers containing unsubstituted TT. Kossmehl et al., Makromol. Chem. 1982, 183, p. 2747 report co-polymers of TT with e.g. a vinylene linker group. However, these polymers were poorly soluble and their electrical characterisation was not reported. Rutherford et al., Macromolecules, 1992, 125, p. 2294 reports the synthesis of TT with alkynyl linkers and of electropolymerised unsubstituted or monomethylated TT. Again all such polymers were insoluble.

WO 99/12989 discloses oligomers and polymers comprising two or more fused thiophene rings which may be substituted or unsubstituted for use in TFTs and FETs. However, there is no specific disclosure of (co)polymers of disubstituted TT or their preparation.

Thus, another aim of the invention is to provide thieno[3,2-b]thiophene (TT) materials that are more easily processible in the manufacture of semiconductor devices, have higher stability and allow easier synthesis also at large scale compared to TT materials of prior art.

It was found that the above aims can be achieved by providing monomers, oligomers and (co)polymers according to the present invention.

SUMMARY OF THE INVENTION

The invention relates to mono-, oligo- and polymers comprising at least one thieno[3,2-b]thiophene-2,5-diyl (TT) group, characterized in that they comprise at least one TT group that is substituted in 3- and 6-position and/or at least one thiophene-2,5-diyl or selenophene-2,5-diyl group that is substituted in 3- and/or 4-position.

The invention further relates to a semiconductor or charge transport material, component or device comprising at least one mono-, oligo- or polymer as defined above.

The invention further relates to the use of polymers according to the invention as charge-transport, semiconducting, electrically conducting, photoconducting or light-emitting material in optical, electrooptical or electronic components or devices, organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, photovoltaic or sensor devices, charge injection layers, Schottky diodes, planarising layers, antistatic films, conducting substrates or patterns, electrode materials in batteries, photoconductors, electrophotographic applications, electrophotographic recording, organic memory devices, alignment layers, cosmetic or pharmaceutical compositions, or for detecting and discriminating DNA sequences.

The invention further relates to an optical, electrooptical or electronic device, FET, integrated circuit (IC), TFT, OLED or alignment layer comprising a semiconducting or charge transport material, component or device according to the invention.

The invention further relates to a TFT or TFT array for flat panel displays, radio frequency identification (RFID) tag, electroluminescent display or backlight comprising a semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

The mono-, oligo and polymers according to the invention are especially useful as charge transport semiconductors because they have high carrier mobilities. One reason for this improvement in charge carrier mobility is the enhanced planarity and conjugation of the fused ring system, in addition to the higher concentration of sulfur atoms per unit length. For example TT has three double bonds and two sulfur atoms per molecules, whilst thiophene has two double bonds and one sulfur atom, and 2,2-bithiophene has four double bonds and two sulfur atoms per molecule.

Copolymerisation of TT with functionalised aromatic or unsaturated comonomers can further improve the solubility and the charge transport properties. Variation of the aromatic comonomers provides a method of tailoring the band gap of the polymers. This leads to better stability and higher charge carrier mobility.

Compounds according to the present invention comprising disubstituted TT groups are especially preferred. The direct polymerisation of unsubstituted TT's often affords insoluble polymers, they should therefore be polymerised with a co-monomer bearing solubilising groups in order to provide polymers of good solubility. Mono-substituted TT's can be directly polymerised to afford soluble polymers, however, especially in case of homopolymers the orientation of the substituent on each TT must be carefully controlled with respect to the adjacent substituted TT to ensure high regioregularity. High regioregularity has been shown in the case of mono-substituted thiophene to be essential to provide a material with good charge carrier mobility. However, the synthesis of highly regioregular materials is non-trivial and affords extra complexity and expense to the synthesis of such polymers.

Especially preferred are polymers wherein the TT group is substituted by two alkyl or fluoroalkyl groups. The introduction of fluoroalkyl and alkyl side chains into the TT group improves their solubility and therefore their solution processibility. Furthermore, the presence of fluoroalkyl side chains also renders these materials effective as n-type semiconductors. The electron-withdrawing nature of the fluoroalkyl substituents will also lower the HOMO further and result in a more stable material, which is less susceptible to oxidation.

Particularly preferred are compounds of formula I

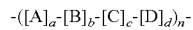

$-([A]_a\text{-}[B]_b\text{-}[C]_c\text{-}[D]_d)_n-$      I wherein

A and C are independently of one another

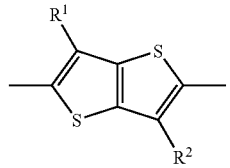

B and D are independently of one another $-CX^1=CX^2-$, $-C\equiv C-$ or an arylene or heteroarylene group that is optionally substituted with one or more groups $R^1$, $R^1$ and $R^2$ independently of each other denote H, halogen, aryl or heteroaryl which are optionally substituted, or straight chain, branched or cyclic alkyl with 1 to 20 C-atoms, which may be unsubstituted, mono- or polysubstituted by F, Cl, Br, I or CN, and wherein one or more non-adjacent $CH_2$ groups are optionally replaced, in each case independently from one another, by $-O-$, $-S-$, $-NH-$, $-NR^0-$, $-SiR^0R^{00}-$, $-CO-$, $-COO-$, $-OCO-$, $-O-CO-O-$, $-S-CO-$, $-CO-S-$, $-CX^1=CX^2-$ or $-C\equiv C-$ in such a manner that O and/or S atoms are not linked directly to one another, $X^1$ and $X^2$ are independently of each other H, F, Cl or CN, $R^0$ and $R^{00}$ are independently of each other H, alkyl with 1 to 12 C-atoms or aryl, a and c are independently of each other 0 or 1, wherein in at least one group $[(A)_a\text{-}(B)_b\text{-}(C)_c\text{-}(D)_d]$ a and/or c is 1, b and d are independently of each other 0, 1 or 2, n is an integer $\geq 1$, preferably from 1 to 10,000, wherein in case n>1 the groups $[(A)_a\text{-}(B)_b\text{-}(C)_c\text{-}(D)_d]$ can be identical or different, and with the provisos that a) the compounds comprise at least one group A or C that is substituted by groups $R^1$ and $R^2$ each having at least 3 C-atoms, and/or b) the compounds comprise at least one group B or D that is thiophene-2,5-diyl or selenophene-2,5-diyl substituted in 3- and/or 4-position by a group $R^1$ being different from H.

The compounds of formula I are preferably selected of formula I1

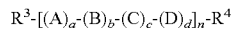

$R^3\text{-}[(A)_a\text{-}(B)_b\text{-}(C)_c\text{-}(D)_d]_n\text{-}R^4$      I1 wherein $R^1$, $R^2$, a, b, c, d and n have independently of each other one of the meanings of formula I, $R^3$ and $R^4$ are independently of each other H, halogen, $C_1$-$C_{12}$-alkyl, $Sn(R^0)_3$, $B(OR^0)_2$, $CH_2Cl$, $COH$, $CH=CH_2$, $SiR^0R^{00}R^{000}$, or optionally substituted aryl or heteroaryl, $R^{000}$ has one of the meanings given for $R^{00}$ in formula I, and $R^0$ and $R^{00}$ have the meanings of formula I.

$R^3$ and $R^4$ are hereinafter also referred to as "terminal groups".

Especially preferred are oligo- and poymers of formula I and I1 (i.e. wherein n>1) having identical recurring units $[(A)_a\text{-}(B)_b\text{-}(C)_c\text{-}(D)_d]$.

Further preferred are compounds of formula I and I1 wherein $R^1$ and $R^2$ are identical groups.

Especially preferred are oligo- and polymers, in particular those of formula I and I1, having a degree of polymerisation (n in formula I) from 2 to 5000, in particular from 10 to 5000, very preferably from 20 to 1000.

Further preferred are oligo- and polymers, in particular those of formula I and II, having a molecular weight from 5000 to 300,000, in particular from 10,000 to 100,000.

In the oligo- and polymers of the present invention the groups $[(A)_a\text{-}(B)_b\text{-}(C)_c\text{-}(D)_d]$ can be selected of formula I independently of each other, so that an oligo- or polymer may comprise identical or different recurring units $[(A)_a\text{-}(B)_b\text{-}(C)_c\text{-}(D)_d]$. The oligo- and polymers thus include homopolymers and copolymers like for example

- statistically random copolymers, for example with a monomer sequence such as -A-B-B-C-B-D-A-B-D- or -A-C-A-A-C-,
- alternating copolymers, for example with a monomer sequence such as -A-B-A-B-A-B-A-B-, -A-B-C-A-B-C- or -A-B-C-D-A-B-C-D, which can also be regarded as homopolymers of the monomer units (A-B), (A-B-C) and (A-B-C-D), respectively, or with a monomer sequence such as -(A-B-C)-(A-B)-(A-B-C)-(A-B)-, and
- block copolymers, for example with a monomer sequence such as -A-A-B-B-B-B-C-C-C-D-D-D- (if A, B, C and D are regarded as monomer units) or with a monomer sequence such as -(A-B)-(A-B)-(A-B)-(A-B-C)-(A-B-C)-(A-B-C)-(A-B-C) (if e.g. (A-B), and (A-B-C) are regarded as monomer units), wherein the groups A, B, C and D preferably together form a conjugated system, and wherein in addition groups occurring more than once (for example each group B in the sequence -B-B-B-B-B-) can be identical or different from one another.

Especially preferred are polymers of the formula $(A\text{-}B)_n$, $(A\text{-}B\text{-}C)_n$, $(A\text{-}B\text{-}D)_n$, $(A\text{-}C\text{-}D)_n$, $(B\text{-}C\text{-}D)_n$ or $(A\text{-}B\text{-}C\text{-}D)_n$ consisting of identical recurring units.

Preferably the groups A, B, C and D together form a conjugated system.

Further preferred are regioregular polymers of formula I and I1, in particular with a high regioregularity of head-to-tail (HT) couplings.

The regioregularity in these polymers is preferably at least 90%, in particular 95% or more, very preferably 98% or more, most preferably from 99 to 100%.

Regioregular polymers are advantageous as they show strong interchain pi-pi-stacking interactions and a high degree of crystallinity, making them effective charge transport materials with high carrier mobilities.

Further preferred are polymers comprising symmetrical recurring units, in particular homopolymers of symmetrical 3,6-disubstituted TT-2,5-diyl monomers, wherein regioregularity is not an issue.

Further preferred are mono-, oligo- and polymers of formula I and I1 wherein b is 1 and B is thiophene-2,5-diyl or selenophene-2,5-diyl that is optionally substituted by one or two groups $R^1$ different from H, $R^1$ and $R^2$ are selected from $C_3\text{-}C_{20}$-alkyl that is optionally substituted with one or more fluorine atoms, $C_3\text{-}C_{20}$-alkenyl, $C_3\text{-}C_{20}$-alkynyl, $C_3\text{-}C_{20}$-ester, $C_3\text{-}C_{20}$-amino, $C_3\text{-}C_{20}$-fluoroalkyl, and optionally substituted aryl or heteroaryl, very preferably $C_3\text{-}C_{20}$-alkyl or $C_3\text{-}C_{20}$-fluoroalkyl, $R^3$ and $R^4$ are selected from H, $C_1\text{-}C_{12}$-alkyl, halogen, $Sn(R^0)_3$, $B(OR^0)_2CH_2Cl$, $CH_2OH$, $CH\!=\!CH_2$, $SiR^0R^{00}R^{000}$ and optionally substituted aryl or heteroaryl, P* is —OH or —O—Si—$R^0R^{00}R^{000}$, preferably wherein $R^0$, $R^{00}$ and $R^{000}$ are identical or different groups selected from aryl or $C_{1\text{-}12}$-alkyl, preferably $C_1\text{-}C_6$-alkyl, like methyl, ethyl, isopropyl, tert-butyl or phenyl, n>1.

If B or D is arylene or heteroarylene, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another.

Preferred arylene or heteroarylene groups are selected from phenylene in which, in addition, one or more CH groups may be replaced by N, or naphthalene, alkyl fluorene or oxazole, thiophene, selenophene, dithienothiophene, wherein all these groups are optionally mono- or polysubstituted with L as defined above.

Especially preferred arylene or heteroarylene groups groups are 1,4-phenylene, fluorinated 1,4-phenylene, 2,5-pyridine, 2,5-pyrimidine, p,p'-biphenyl, naphthalene-2,6-diyl, thiophene-2,5-diyl, selenophene-2,5-diyl, fluorinated or alkylated thiophene-2,5-diyl or selenophene-2,5-diyl, 2,2'-dithiophene, fluorinated or alkylated 2,2'-dithiophene, fluorinated benzo[1,2-b:4,5-b']dithiophene, 2,5-thiazole, 2,5-thiadiazole, 2,5-oxazole and 2,5-oxadiazole, all of which are unsubstituted, mono- or polysubstituted with L as defined above.

If one of $R^{1-4}$ is aryl or heteroaryl, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, OCO—, —OCO—O, —S—CO—, —CO—S—, —CH=CH— or —C≡C— in such a manner that O and/or S atoms are not linked directly to one another.

Especially preferred aryl and heteroaryl groups are phenyl, fluorinated phenyl, pyridine, pyrimidine, biphenyl, naphthalene, thiophene, selenophene, fluorinated thiophene, benzo[1,2-b:4,5-b']dithiophene, thiazole and oxazole, all of which are unsubstituted, mono- or polysubstituted with L as defined above.

If one of $R^{1-4}$ is an alkyl or alkoxy radical, i.e. where the terminal $CH_2$ group is replaced by —O—, this may be straight-chain or branched. It is preferably straight-chain, has 3 to 8 carbon atoms and accordingly is preferably propyl, butyl, pentyl, hexyl, heptyl, octyl, propoxy, butoxy, pentoxy, hexyloxy, heptoxy, or octoxy, furthermore nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain (O)$C_iF_{2i+1}$, wherein i is an integer from 1 to 20, in particular from 3 to 15, very preferably (O)$C_3F_7$, (O)$C_4F_9$, (O)$C_5F_{11}$, (O)$C_6F_{13}$, (O)$C_7F_{15}$ or (O)$C_8F_{17}$, most preferably (O)$C_6F_{13}$.

$CX^1$=$CX^2$ is preferably —CH=CH—, —CH=CF—, —CF=CH—, —CF=CF—, —CH=C(CN)— or —C(CN)=CH—.

Halogen is preferably F, Br or Cl.

Hetero atoms are preferably selected from N, O and S.

Especially preferred are compounds of formula I and I1 wherein -[(A)$_a$-(B)$_b$-(C)$_c$-(D)$_d$]$_n$- is selected from the following formulae

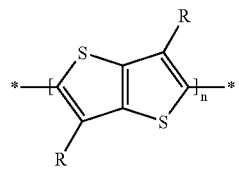
Ia

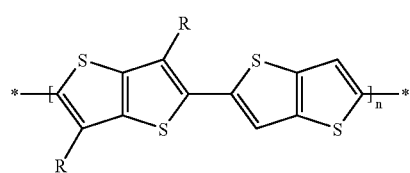
Ib

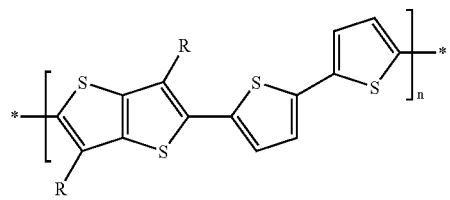
Ic

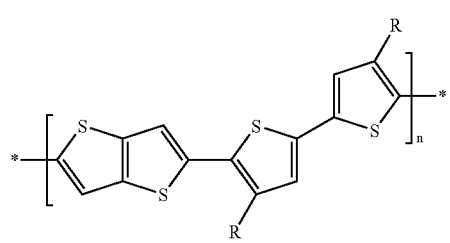
Id

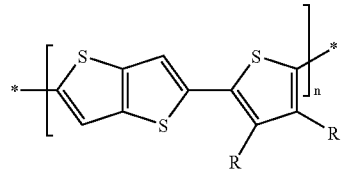
Ie

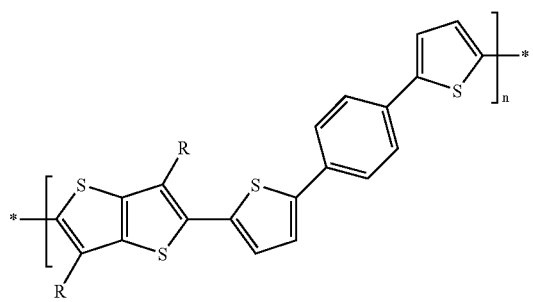
If

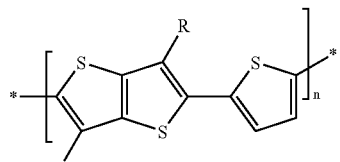
Ig

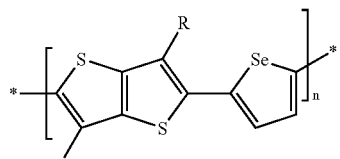
Ih wherein n has one of the meanings of formula I and R has one of the meanings of $R^1$ given in formula I or one of the preferred meanings given above and below, and is preferably different from H.

Mono-, oligo and polymers comprising a disubstituted TT group and an optionally substituted thieno[2,3-b]thiophene group, like for example those of the following formulae

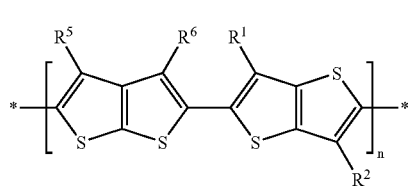
Ia*

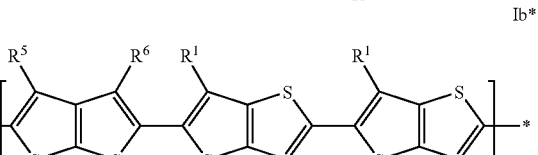
Ib*

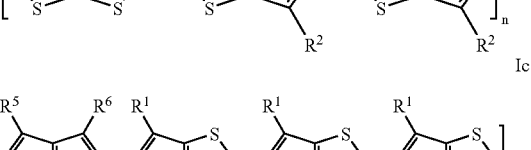
Ic*

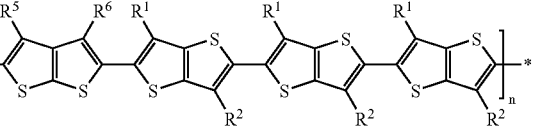

wherein $R^1$ and $R^2$ have one of the meanings of formula I different from H, and $R^5$ and $R^6$ have one of the meanings of $R^1$ as defined above, are less preferred.

The compounds of the present invention can be synthesized according to or in analogy to known methods or to the methods described below. Further methods can be taken from the examples.

Part A: Synthesis of
3,6-dialkyl-thieno[3,2-b]thiophene

With the exception of 3,6-dimethyl, the preparation of 3,6-dialkylated TTs has not been reported in prior art. A one-pot procedure to 3,6-dimethylated thieno[3,2-b] thiophene as shown in Scheme I below has been reported by Nakayama et al., Heterocycles 1994, 38, p 143. However, this method has the disadvantage that it is not amenable to the preparation of longer chain alkyl derivatives, due the mechanism of ring closure. However, the incorporation of longer alkyl chains is desired to provide solution processable polymers.

Scheme 1: Preparation of dimethyl-thieno[3,2-b]thiophene (prior art)

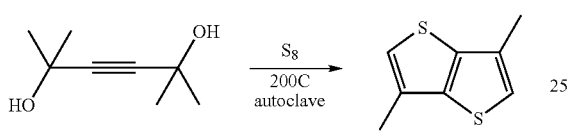

The synthesis of thieno[3,2-b]thiophene (1) (R=H) as depicted in Scheme 2 has been reported in Fuller et al., J. Chem. Soc. Perkin Trans. 1997, 1, 3465-70. The same reference also reports a procedure for the preparation of 3,6-dibromothieno[3,2-b]thiophene (2), via tetrabromination and reduction of the thieno[3,2-b]thiophene core as shown in Scheme 3. The dibromo intermediate (2) is converted into thioalkyl (—SR) derivatives via lithiation and subsequent reaction with electrophillic disulfides. However, thioethers are undesired in the present case because the electron rich nature of these side chains affords polymers that are oxidatively unstable. Moreover long chain alkyl derivatives could not be incorporated by an analogous route due to the low reactivity of alkyl halides which prevented reaction at low temperatare. At temperatures greater than −78° C. the dilithium salt of (2) ring opens (see Fuller et al J. Chem. Soc. Perkin Trans. 1999, 1, p 1273) to afford non-fused products.

Scheme 2: Synthesis of thieno-[3,2-b]thiophene (prior art)

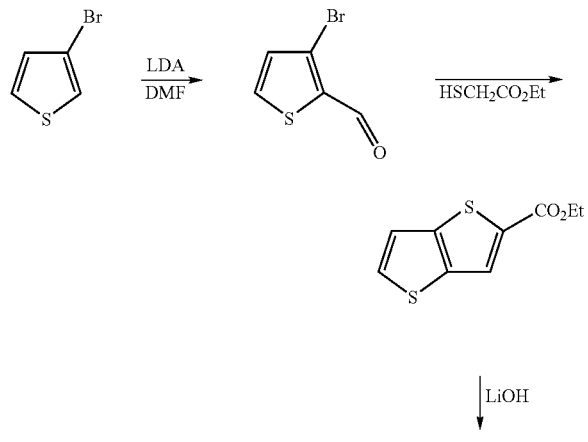

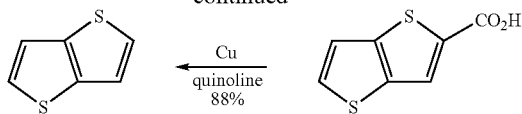

Scheme 3: Preparation of 3,6-dialkylthienothiophene via dibromo intermediate (prior art)

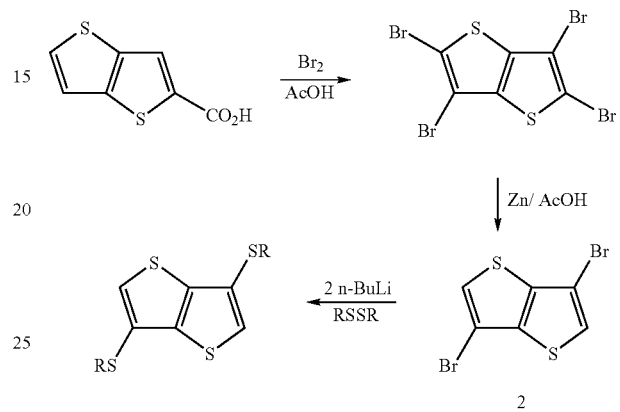

A preferred synthesis of 3,6-dialkylthieno[3,2-b] thiophene according to the present invention is exemplarily described in scheme 4, utilising dibromo intermediate (2). Cross coupling of (2) with organozinc reagents in the presence of a bidentate palladium catalyst (such as Pd(dppf)Cl$_2$) is found to occur in excellent yields under microwave heating. Thus heating octylzinc bromide, 3,6-dibromothieno[3,2-b] thiophene and Pd(dppf)Cl$_2$ in THF at 140° C. for 7 min afforded a 95% yield of 3,6-dioctylthieno[3,2-b]thiophene.

Scheme 4

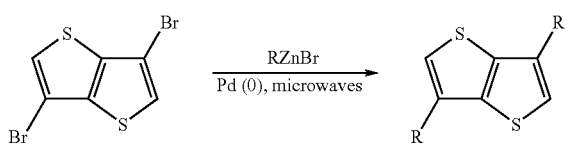

Part B: Polymers Containing
3,6-dialkylthienothiophene 3,6-Dimethyl thieno[3,2-b]thiophene has been polymerised by electropolymerisation methods to give an insoluble polymer (J. Appl. Electrochemistry; 2001; 31, p 839). However, such a polymer is not suitable for the applications according to the present invention.

Dimers, trimers and tetramers of 3,6-dimethyl thieno[3,2-b]thiophene have been described by Nakayama et al (Tetrahedron, 1996, 52, p 471). Again the tetramers are of very low solubility and no electrical properties are reported.

According to the present invention, homo-(3) and co-polymers of 3,6-dioctyl thieno[3,2-b]thiophene are preferably prepared as shown in Scheme 5. Such polymers are highly soluble in organic solvents and can be readily processed into thin films.

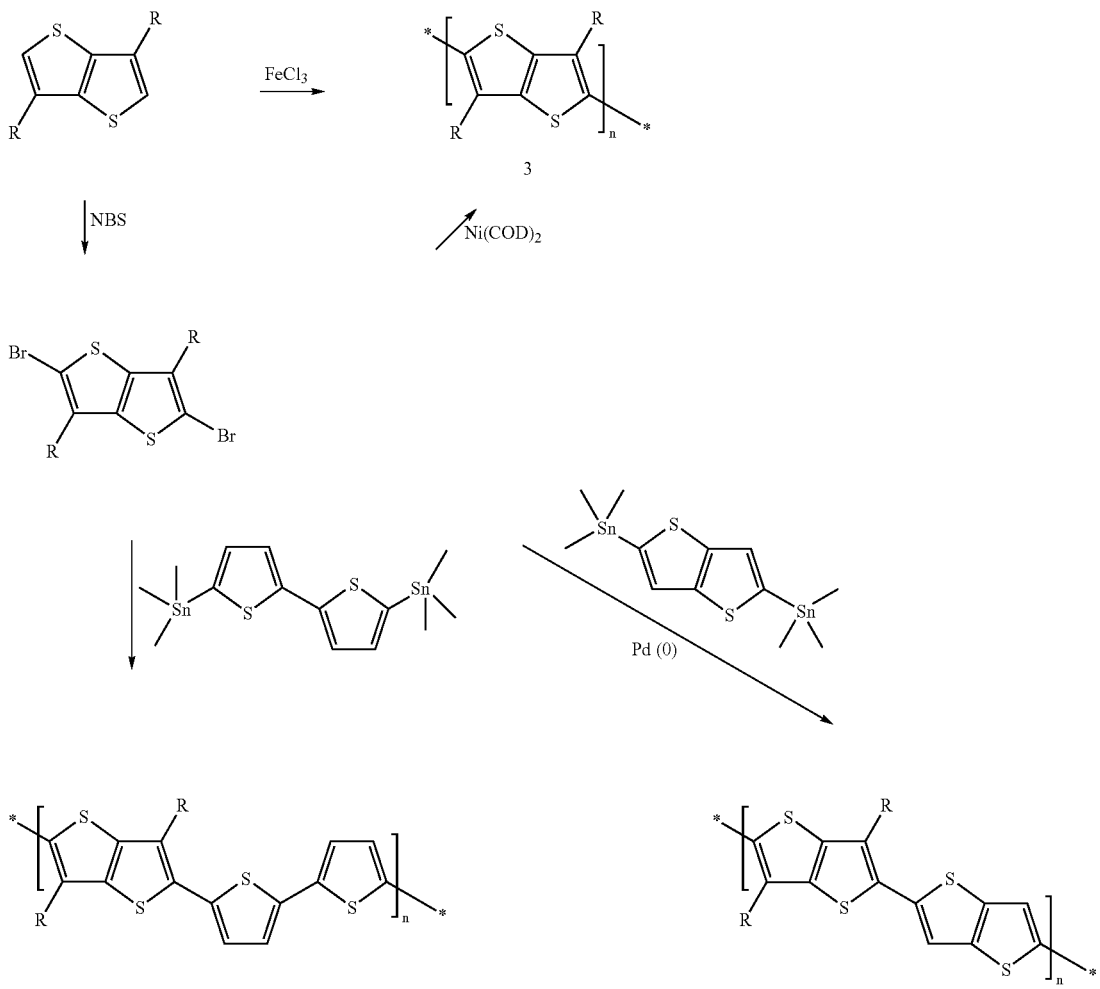

Scheme 5

Part C: Polymers Containing Unsubstituted thieno[3,2-b]thiophene

There are some reports of polymers containing unsubstituted TT. Kossmehl et al., Makromol Chem. 1982, 183, p. 2747 reported co-polymers of TT with a vinylene linker group (4). However, such polymers were poorly soluble and their electrical characterisation was not reported.

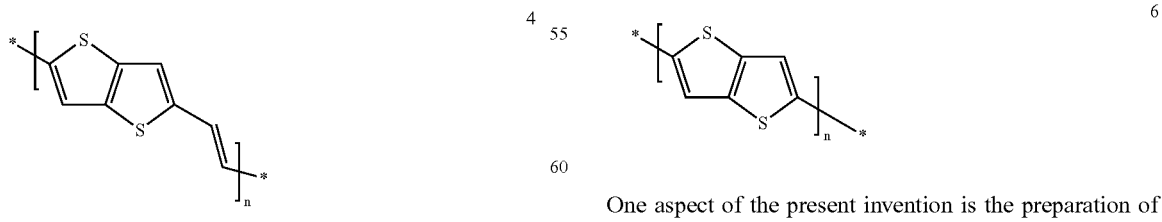

Rutherford et al., Macromolecules, 1992, 125, p. 2294 reported the synthesis of TT with alkynyl linkers (5) and the electropolymerisation of unsubstituted TT to give (6). Again all such polymers were insoluble.

One aspect of the present invention is the preparation of co-polymers of unsubstituted thieno[3,2-b]thiophene with alkylated thiophenes. Such polymers are readily soluble in organic solvents, and the alkyl side chains can readily pack to afford closely packed structures. Such structures are beneficial to charge transport. The polymers (7) are readily synthesised by Stille coupling as shown in Scheme 6. The Stille coupling has previously been used to prepare conjugated polymers (see Babudri et al, *J. Mater. Chem.*, 2004, 14, p 11-34).

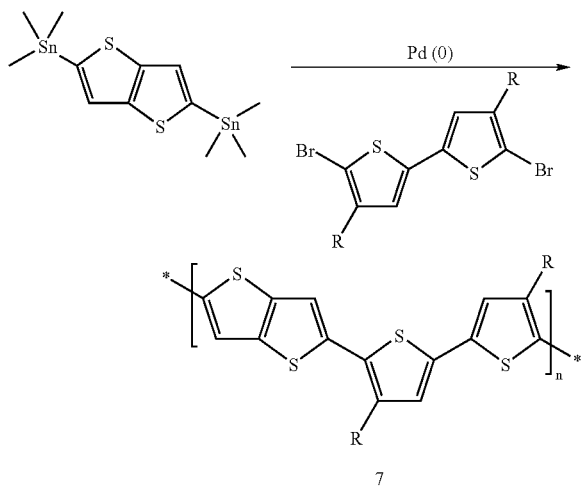

Scheme 6

Polymer (7) exhibits good transistor characteristics with a charge carrier mobility ($\mu$) of 0.02 cm$^2$/vs (unoptimised).

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g., from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, La $(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

A preferred embodiment of the present invention relates to mono-, oligo- and polymers of formula I and its preferred subformulae that are mesogenic or liquid crystalline. These materials are particularly useful as semiconductors or charge transport materials, as they can be aligned into uniform highly ordered orientation in their liquid crystal phase by known techniques, thus exhibiting a higher degree of order that leads to particularly high charge carrier mobility.

It is also possible to copolymerise the mono-, oligo- and polymers according to the present invention with other mesogenic or liquid crystal monomers that are known from prior art, in order to induce or enhance liquid crystal phase behaviour.

Particularly preferred are liquid crystal materials having a nematic and/or smectic phase. For FET applications smectic materials are especially preferred. For OLED applications nematic or smectic materials are especially preferred. Especially preferred are smectic A ($S_A$) phases, furthermore highly ordered smectic phases like the $S_B$, $S_E$, $S_G$ and $S_F$ phase.

Alignment of liquid crystal materials can be achieved for example by treatment of the substrate onto which the materials are coated, by shearing the material during or after coating, by application of a magnetic or electric field to the coated material, or by the addition of surface-active compounds to the material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

The mono-, oligo- and polymers according to the present invention can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The mono-, oligo- and polymers of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with monetry value, like stamps, tickets, shares, cheques etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835-837.

According to another use, the inventive compounds, materials or films can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials and polymers according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

The polymers and materials according to the present invention can also be used in cosmetic or pharmaceutical compositions, for example in cosmetic compositions for hair treatment as disclosed in EP 1 498 112A2.

The examples below serve to illustrate the invention without limiting it. In the foregoing and the following, all temperatures are given in degrees Celsius, and all percentages are by weight, unless stated otherwise. All reactions are run under nitrogen atmosphere unless otherwise noted. Phase transitions are determined by a mixture of DSC and optical microscopy. $S_x$ and $S_{x1}$ refer to smectic transitions of undetermined nature.

Example 1

Polymer 3 is prepared as described below:

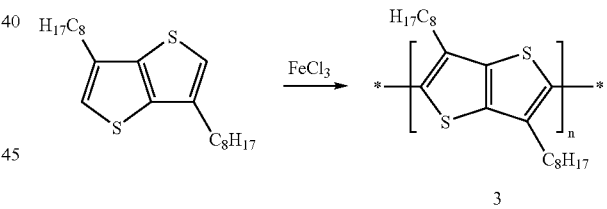

Poly(3,6-dioctylthieno[3,2-b]thiophene) (3)

A 3-necked flask is charged with anhydrous $FeCl_3$ (0.71 g, 4.39 mmol) under nitrogen. Anhydrous chloroform (20 mL) is added to afford a suspension. A solution of 3,6-dioctylthieno[3,2-b]thiophene (0.40 g, 1.10 mmol) in anhydrous chloroform (20 mL) is added to the $FeCl_3$ suspension. The reaction mixture is stirred at RT for 24 h with nitrogen bubbled through the mixture to remove the HCl formed. The reaction mixture is poured into methanol (200 mL). The polymer that precipitates is filtered off and washed with methanol. The polymer is stirred in a 25% ammonia solution (60 mL) for 24 h to de-dope the polymer. The polymer is filtered off and washed with water followed by methanol. The polymer is extracted with methanol (soxhlet) and acetone (soxhlet) for 24 h each. Finally the polymer is dissolved in warm chloroform, filtered and precipitated in methanol. The polymer is collected by centrifugation and dried under vacuum to afford 29 mg of product. GPC(CHCl$_3$) Mn (8,000 g/mol), Mw (52,400 g/mol). $\lambda_{max}$ 348 nm (solid film). $^1$H NMR as expected.

Example 2

Polymer 7 is prepared as described below:

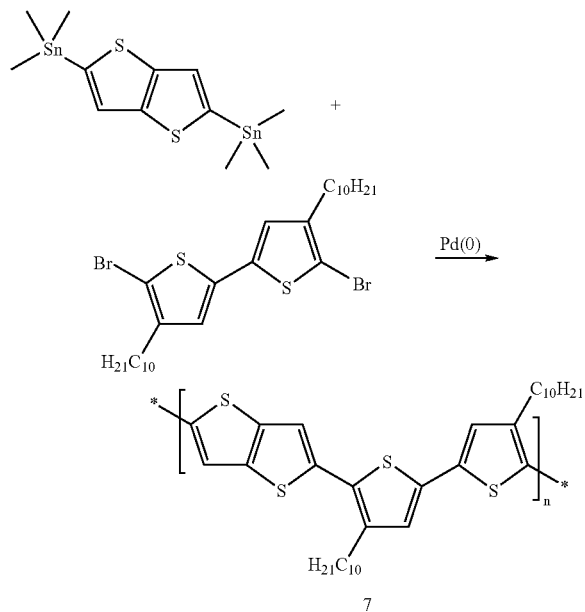

2,5-Bis-trimethylstannylthieno[3,2-b]thiophene

A solution of thieno[3,2-b]thiophene (see Fuller et al., J. Chem. Soc. Perkin Trans. 1997, 1, 3465-70) (2.00 g, 14 mmol) is dissolved in anhydrous THF (100 ml) and cooled to −78° C. under nitrogen. A solution of n-butyllithium (12 ml of a 2.5M solution in hexanes, 30 mmol) is added dropwise over 5 min, and the resulting solution is allowed to warm to 20° C. over 30 min and stirred at that temperature for 3 h. The resulting suspension is cooled to −78° C. and trimethyltin chloride (5.9 g, 30 mmol) is added at once as a solid. The reaction is allowed to warm to RT over 4 h and stirred at that temperature for an additional 20 h. The reaction is quenched by the addition of saturated sodium hydrogen carbonate (100 ml). Ethyl acetate (50 ml) is added and the layers separated. The organic layer is washed with sodium carbonate (80 ml of a 2M aqueous solution) and brine (80 ml), dried (sodium sulfate), filtered and concentrated under reduced pressure. The resulting crude product is dry loaded onto a 20 g reverse phase silica column and eluted with acetonitrile. The first fraction is collected, concentrated and recrystallised from acetonitrile to afford the product as white flakes. M/Z cluster centred at 466 (M$^+$). Found C, 30.9; H, 4.4. Calc. for C$_{12}$H$_{20}$S$_2$Sn$_2$C, 30.9; H, 4.3. $^1$H NMR (300 MHz, CDCl$_3$) δ 7.26 (s, 2H), 0.39 (s, 18H). $^{13}$C NMR (75 MHz, CDCl$_3$) δ 147.5, 141.2, 126.1, −8.2.

5,5'-Dibromo-4,4'-bis(decyl)-2,2'-bithiophene 4,4'-Bis(decyl)-2,2'-bithiophene is prepared in analogy to the published procedure (see M. Zagorska and B. Krische Polymer, 1990, 31, p 1379).

To a solution of 4,4'-bis(decyl)-2,2'-bithiophene (6.60 g, 14.8 mmol) in chloroform (100 ml) and glacial acetic acid (100 ml) at 5° C. in the dark is added N-bromosuccinimde (5.40 g, 30 mmol) portionwise over 1 h. The resulting solution is warmed to 20° C. and stirred for a further 16 h. The solvent is removed under reduced pressure and the residue suspended in MTBE (200 ml). Filtration of the solution removed succinimde byproduct. The filtrate is washed with 5% sodium carbonate (100 ml), water (100 ml) and brine (100 ml), dried (sodium sulfate), filtered and concentrated under reduced pressure. The resulting crude product is further purified by reverse phase column chromatography over RP18 silica (23 g) eluting with acetonitrile/THF 2:1. A final recrystallisation from ethyl acetate afforded the product. HRMS 602.1248 (calc. for C$_{28}$H$_{44}$S$_2$Br$^{79}$$_2$ 602.1251). $^1$H NMR (300 MHz, CDCl$_3$) δ 6.77 (s, 2H), 2.70 (t, 4H), 1.57 (quint, 4H), 1.28 (m, 28H), 0.88 (t, 6H). $^{13}$C NMR (75 MHz, CDCl$_3$) δ 143.0, 136.1, 124.5, 107.9, 31.9, 29.62, 29.57, 29.40, 29.35, 29.2, 22.7, 14.2.

Poly(2,5-bis(3-decylthiophen-2-yl)thieno[3,2-b]thiophene) (7)

A 10 ml glass vial is charged with a stirrer bar, 5,5'-dibromo-4,4'-didecylbithiophene (182 mg, 0.3 mmol), 2,5-bis(trimethylstannyl)-thieno[3,2-b]thiophene (140 mg, 0.3 mmol), tetrakis(triphenylphosphine) palladium (0) (5.0 mg, 1.4 mol %) and chlorobenzene (4.5 ml). The glass vial is purged with nitrogen and securely sealed. The glass vial is placed into a microwave reactor (Emrys Creator, Personal Chemistry Ltd) and heated to 200° C. for 10 minutes. Elapsed time is only calculated once the temperature had been reached. After cooling to RT, the reaction mixture is precipitated into a mixture of methanol (50 ml) and concentrated hydrochloric acid (2 ml) and stirred for 16 h at 20° C. The precipitate is filtered and extracted with methanol (soxhlet) and acetone (soxhlet) for 12 h each. Finally the polymer is dissolved in warm chlorobenzene, filtered and precipitated in methanol. The polymer is collected by centrifugation and dried under vacuum to afford the 92 mg of product. GPC (CHCl$_3$) Mn (8,750 g/mol), Mw (19,200 g/mol). $\lambda_{max}$547 nm (solid film). $^1$H NMR (300 MHz, CDCl$_3$, 50° C.) δ 7.26 (s, 2H), 7.03 (s, 2H), 2.79 (t, 4H), 1.70 (quint, 4H), 1.4-1.20 (m, 28H), 0.88 (t, 6H).

Example 3

Polymer 8 is prepared as described below:

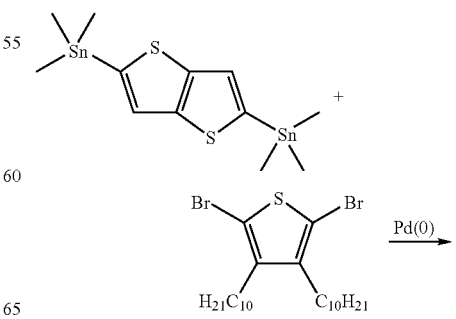

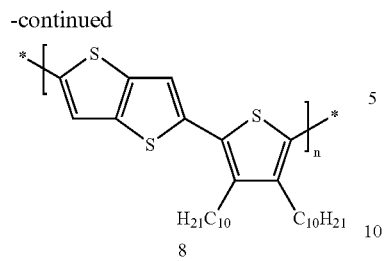

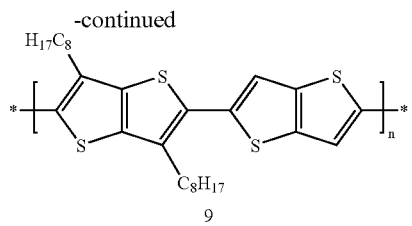

3,6-Dioctylthieno[3,2-b]thiophene

A 20 ml glass vial is charged with a stirrer bar, 3,6-dibromo-thieno[3,2-b]thiophene (see Fuller, L. S.; Iddon, B.; Smith, K. A. *J. Perkin Trans.* 1, 1997, p 3465) (1.0 g, 3.35 mmol) and (1,1'-bis(diphenylphosphino)ferrocene)palladium (II) chloride (10 mg, 0.014 mmol). The glass vial is securely sealed and then purged with nitrogen. THF (2 ml) and octylzinc bromide (16.8 mL of a 0.5M solution in THF) are added, and the reaction stirred for 3 min at 25° C. The mixture is heated in a microwave reactor (Emrys Creator, Personal Chemistry Ltd) at 150° C. for 7 min. The reaction is cooled, diluted with MTBE (20 ml) and washed with 5% HCl (10 ml), water (3×10 ml), brine (10 m), dried (sodium sulfate), filtered and concentrated under reduced pressure. The crude material is further purified by filtration over silica (eluent: petrol), and the resulting waxy solid is recrystallised from ethanol to afford the product as a pale yellow solid. M/Z 364 (M+). Found C, 72.3; H, 9.7, Calc. for $C_{22}H_{36}S_2C$, 72.5; H, 9.9. $^1$H NMR (300 MHz, CDCl$_3$) δ 8.95 (2H, s), 2.70 (4H, t), 1.74 (4H, quint), 1.31 (20H, m), 0.88 (6H, t), $^{13}$C NMR (75 MHz, CDCl$_3$) δ 139.3, 135.5, 120.8, 31.9, 29.8, 29.42, 29.37, 29.2, 28.8, 22.7, 14.1.

2,5-Dibromo-3,6-dioctylthieno[3,2-b]thiophene

To a solution of 3,6-dioctylthieno[3,2-b]thiophene (2.0 g, 5.5 mmol) in glacial acetic acid (50 ml) and chloroform (50 ml) at 5° C. is added N-bromosuccinimide (1.95 g, 11 mmol) portionwise over 1 h. The solution is stirred for a further 24 h at 20° C. The solvent is removed under reduced pressure, and the residue suspended in MTBE (100 ml) and filtered to remove succimide byproduct. The organic filtrate is washed with water (50 ml), 5% Na$_2$CO$_3$ (50 ml) and water (50 ml), dried (sodium sulfate), filtered and concentrated under reduced pressure. The residue is further purified by filtration thorugh silica (eluent: petrol) to afford a yellow oil that crystallised upon standing. HRMS 520.0472 (calc. for $C_{22}H_{34}S_2Br^{79}_2$ 520.0469). $^1$H NMR (300 MHz, CDCl$_3$) δ 2.66 (4H, t), 1.65 (4H, quint), 1.29 (20H, m), 0.87 (6H, t), $^{13}$C NMR (75 MHz, CDCl$_3$) δ 136.1, 134.4, 109.4, 31.9, 29.32, 29.27, 29.19, 28.1, 22.7, 14.1.

Poly(3,6-dioctylthieno[3,2-b]thiophene-co-thieno[3,2-b]thiophene) (9)

A 10 ml glass vial is charged with a stirrer bar, 2,5-dibromo-3,6-dioctylthieno[3,2-b]thiophene (157 mg, 0.3 mmol), 2,5-bis-trimethylstannylthieno[3,2-b]thiophene (140 mg, 0.3 mmol) tetrakis(triphenylphosphine) palladium (0) (5.0 mg, 1.4 mol %) and chlorobenzene (4.5 ml). The glass vial is purged with nitrogen and securely sealed. The glass vial is placed into a microwave reactor (Emrys Creator, Personal Chemistry Ltd) and heated to 200° C. for 10 minutes. Elapsed time is only calculated once the temperature had been reached. After cooling to RT, the reaction mixture is precipitated into a mixture of methanol (50 ml) and concentrated hydrochloric acid (2 ml) and stirred for 16 h at 20° C.

2,5-Dibromo-3,4-didecylthiophene 3,4-Didecylthiophene is prepared in analogy to the published procedure (see S. Destri, M. Pasini, C. Pelizzi, W. Porzio, G. Predieri, C. Vignali *Macromolecules*, 1999, 32, p 353). 2,5-Dibromo-3,4-didecylthiophene is prepared from 3,4-didecylthiophene in analogy to the published procedure (see P. Bäuerle, F. Pfau, H. Schlupp, F. Würthner, K. U. Gaudl, M. B. Caro, P. Fischer *J. Chem. Soc., Perkin Trans.* 2, 1993, p 489).

Poly(3,4-didecylthiophene-co-thieno[3,2-b]thiophene) (8)

A 10 ml glass vial is charged with a stirrer bar, 2,5-dibromo-3,4-didecylthiophene (157 mg, 0.3 mmol), 2,5-bis(trimethylstannyl)-thieno[3,2-b]thiophene (140 mg, 0.3 mmol), tetrakis(triphenylphosphine) palladium (0) (5.0 mg, 1.4 mol %) and chlorobenzene (4.5 ml). The glass vial is purged with nitrogen and securely sealed. The glass vial is placed into a microwave reactor (Emrys Creator, Personal Chemistry Ltd) and heated to 200° C. for 10 minutes. After cooling to RT, the reaction mixture is precipitated into a mixture of methanol (20 ml) and 37% hydrochloric acid (2 ml), and stirred for 48 h at 20° C. The polymer is filtered off, washed with methanol, and dried under vacuum. The polymer is washed (via Soxhlet extraction) with methanol for 24 h and acetone for 24 h, and dried under vacuum to afford the product as a orange solid. GPC(CHCl$_3$) Mn (13,000 g/mol), Mw (24,700 g/mol). $λ_{max}$482 nm (solid film). $^1$H NMR as expected.

Example 4

Polymer 9 is prepared as described below:

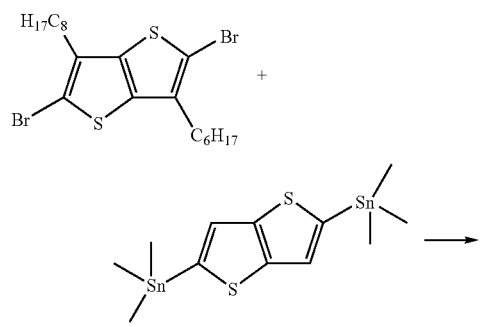

The precipitate is filtered and extracted with methanol (soxhlet) and acetone (soxhlet) for 12 h each. Finally the polymer is dissolved in warm chlorobenzene, filtered and precipitated in methanol. The polymer is collected by centrifugation and dried under vacuum to afford the 132 mg of product. GPC(CHCl$_3$) Mn (3,200 g/mol), Mw (4,500 g/mol). $\lambda_{max}$445 nm (solid film). $^1$H NMR as expected.

Example 5

Polymer 10 is prepared as described below:

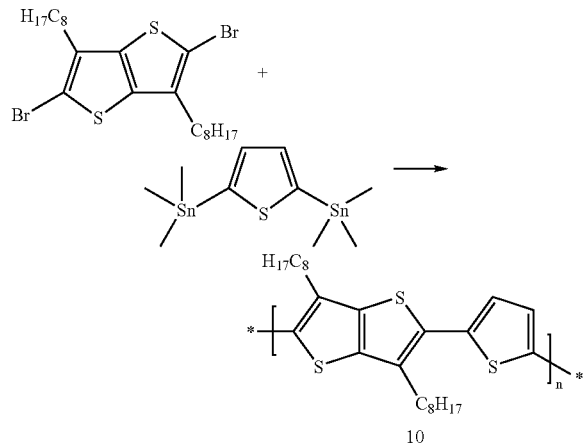

Poly(3,6-dioctylthieno[3,2-b]thiophene-co-thiophene) (9)

A 10 ml glass vial is charged with a stirrer bar, 2,5-dibromo-3,6-dioctylthieno[3,2-b]thiophene (157 mg, 0.3 mmol), 2,5-bis-(trimethylstannyl)thiophene (123 mg, 0.3 mmol), tetrakis(triphenylphosphine) palladium (0) (5.0 mg, 1.4 mol %) and chlorobenzene (4.5 ml). The glass vial is purged with nitrogen and securely sealed. The glass vial is placed into a microwave reactor (Emrys Creator, Personal Chemistry Ltd) and heated to 200° C. for 10 minutes. Elapsed time is only calculated once the temperature had been reached. After cooling to RT, the reaction mixture is precipitated into a mixture of methanol (50 ml) and concentrated hydrochloric acid (2 ml) and stirred for 16 h at 20° C. The precipitate is filtered and extracted with methanol (soxhlet) and acetone (soxhlet) for 12 h each, and then dried under vacuum to afford 102 mg of product. GPC(CHCl$_3$) Mn (8,800 g/mol), Mw (20,800 g/mol). $\lambda_{max}$528 nm (solid film). $^1$H NMR (300 MHz, CDCl$_3$, 50° C.) δ 7.16 (s, 2H), 3.00 (br t, 4H), 1.80 (m, 4H), 1.40-1.20 (m, 20H), 0.90 (t, 6H).

Example 6

Polymer 11 is prepared as described below:

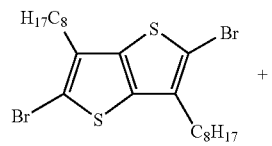

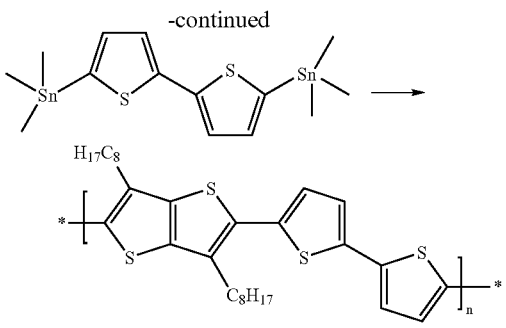

Poly(3,6-dioctylthieno[3,2-b]thiophene-co-bithiophene) (11)

A 10 ml glass vial is charged with a stirrer bar, 2,5-dibromo-3,6-dioctylthieno[3,2-b]thiophene (157 mg, 0.3 mmol), 5,5'-bis(trimethylstannyl)-[2,2']-bithiophene (148 mg, 0.3 mmol), tetrakis(triphenylphosphine) palladium (0) (5.0 mg, 1.4 mol %) and chlorobenzene (4.5 ml). The glass vial is purged with nitrogen and securely sealed. The glass vial is placed into a microwave reactor (Emrys Creator, Personal Chemistry Ltd) and heated to 200° C. for 10 minutes. Elapsed time is only calculated once the temperature had been reached. After cooling to RT, the reaction mixture is precipitated into a mixture of methanol (50 ml) and concentrated hydrochloric acid (2 ml) and stirred for 16 h at 20° C. The precipitate is filtered and extracted with methanol (soxhlet) and acetone (soxhlet) for 12 h each. Finally the polymer is dissolved in warm chlorobenzene, filtered and precipitated in methanol. The polymer is collected by centrifugation and dried under vacuum to afford 144 mg of product. GPC(CHCl$_3$) Mn (6,000 g/mol), Mw (10,000 g/mol). $\lambda_{max}$511 nm (solid film). $^1$H NMR as expected.

Example 7

Polymer 12 is prepared as described below:

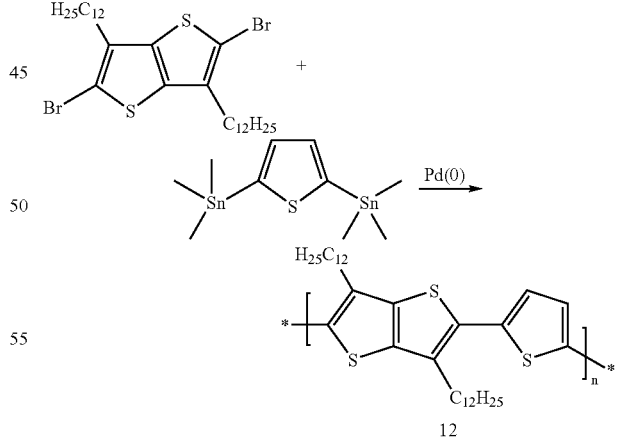

3,6-Didodecylthieno[3,2-b]thiophene

A 20 mL glass vial is charged with 3,6-dibromothieno[3,2-b]thiophene (1.00 g, 3.36 mmol) and Pd(dppf)Cl$_2$ (0.14 g, 0.17 mmol, 5 mol %), and purged with nitrogen for 10 minutes. A 0.5M solution of dodecylzinc bromide in anhydrous THF (15 mL, 7.5 mmol) is added. The glass vial is placed into a microwave reactor (Emrys Creator, Personal Chemistry Ltd) and heated at 150° C. for 10 minutes with stirring. After cooling to RT, the reaction mixture is diluted with diethyl ether (100 mL) and quenched with 5% hydrochloric acid (50 mL). The organic layer is separated and the aqueous layer is re-extracted with diethyl ether (100 mL). The combined extracts are washed with water (2×50 mL), dried over sodium sulphate, and concentrated in vacuo. The crude product is filtered through a short plug of silica, eluting with petroleum ether 40-60. Recrystallisation from 2-butanone yielded the product as a pale yellow solid. $^1$H NMR (300 MHz, CDCl$_3$) δ 6.95 (s, 2H), 2.70 (t, 4H), 1.74 (m, 4H), 1.22-1.42 (br, 36H), 0.88 (t, 6H). $^{13}$C NMR (75 MHz, CDCl$_3$) δ 139.3, 135.5, 120.8, 31.9, 29.8, 29.69, 29.67, 29.6, 29.42, 29.37, 28.7, 22.7, 14.2.

2,5-Dibromo-3,6-didodecylthieno[3,2-b]thiophene

A 3-necked flask is charged with 3,6-didodecylthieno[3,2-b]thiophene (2.00 g, 4.19 mmol) and purged with nitrogen. Anhydrous THF (20 mL) is added and the solution is cooled to 0° C. NBS (1.57 g, 8.81 mmol) is added in portions over a period of 20 minutes. The reaction mixture is stirred at 0° C. for 1 h and then at RT for 16 h. The reaction mixture is poured into petroleum ether 40-60 (200 mL) and the precipitate is filtered off. The filtrate is concentrated in vacuo to yield the crude product. Purification by column chromatography (eluent: petroleum ether 40-60) followed by recrystallisation from 2-butanone afforded the product as a white solid. $^1$H NMR (300 MHz, CDCl$_3$) δ 2.67 (t, 4H), 1.66 (m, 4H), 1.22-1.42 (br, 36H), 0.88 (t, 6H). $^{13}$C NMR (75 MHz, CDCl$_3$) δ 136.1, 134.4, 109.4, 31.9, 29.67, 29.65, 29.5, 29.37, 29.34, 29.26, 28.9, 28.1, 22.7, 14.2.

Poly(3,6-didodecylthieno[3,2-b]thiophene-co-thiophene) (12)

A 10 mL glass vial is charged with a stirrer bar, 2,5-dibromo-3,6-didodecylthieno[3,2-b]thiophene (127 mg, 0.2 mmol), 2,5-bis(trimethylstannyl)thiophene (82 mg, 0.2 mmol), Pd$_2$(dba)$_3$ (4 mg, 0.004 mmol, 4 mol % Pd), P(o-tol)$_3$ (3 mg, 0.010 mmol, 5 mol %), LiCl (9 mg, 0.2 mmol) and chlorobenzene (5 mL). The glass vial is purged with nitrogen and securely sealed. The glass vial is placed into a microwave reactor (Emrys Creator, Personal Chemistry Ltd) and heated at 200° C. for 10 minutes with stirring. After cooling to RT, the reaction mixture is precipitated into a mixture of acetone (50 mL) and 37% hydrochloric acid (5 mL), and stirred for 1 h. The polymer is filtered off, washed with acetone, and dried under vacuum. The polymer is washed (via Soxhlet extraction) with acetone for 18 h and petroleum ether 40-60 for 6 h, and dried under vacuum to afford the product as a dark red solid (100 mg, 89%). GPC(CHCl$_3$) Mn (8,100 g/mol), Mw (16,500 g/mol). λ$_{max}$ 550 nm (solid film). $^1$H NMR as expected.

Example 8

Polymer 13 is prepared as described below:

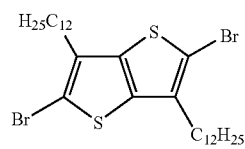

+

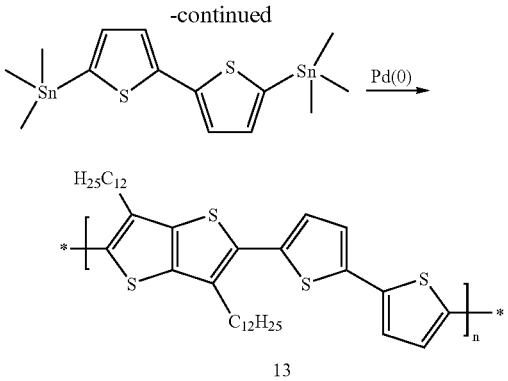

Poly(3,6-didodecylthieno[3,2-b]thiophene-co-bithiophene) (13)

A 10 mL glass vial is charged with a stirrer bar, 2,2'-dibromo-3,3-didodecylthieno[3,2-b]thiophene (127 mg, 0.2 mmol), 5,5'-bis(trimethylstannyl)-2,2'-bithiophene (98 mg, 0.2 mmol), Pd$_2$(dba)$_3$ (4 mg, 0.004 mmol, 4 mol % Pd), P(o-tol)$_3$ (3 mg, 0.010 mmol, 5 mol %), LiCl (9 mg, 0.2 mmol) and chlorobenzene (5 mL). The glass vial is purged with nitrogen and securely sealed. The glass vial is placed into a microwave reactor (Emrys Creator, Personal Chemistry Ltd) and heated at 200° C. for 10 minutes with stirring. After cooling to RT, the reaction mixture is precipitated into a mixture of acetone (50 mL) and 37% hydrochloric acid (5 mL), and stirred for 1 h. The polymer is filtered off, washed with acetone, and dried under vacuum. The polymer is washed (via Soxhlet extraction) with acetone for 18 h and petroleum ether 40-60 for 6 h, and dried under vacuum to afford the product as a dark red solid (96 mg, 75%). GPC (CHCl$_3$) Mn (9,300 g/mol), Mw (16,000 g/mol). λ$_{max}$ 530 nm (solid film). $^1$H NMR as expected.

Example 9

Polymer 14 is prepared as described below:

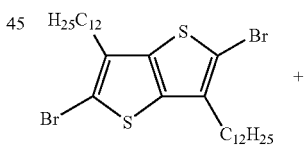

+

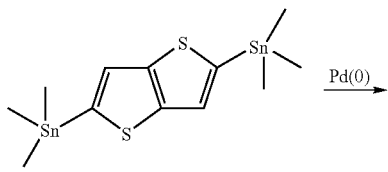

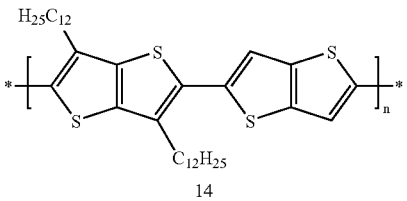

Poly(3,6-didodecylthieno[3,2-b]thiophene-co-thieno[3,2-b]thiophene) (14)

A 10 ml glass vial is charged with a stirrer bar, 2,5-dibromo-3,6-didodecylthieno[3,2-b]thiophene (127 mg, 0.2 mmol), 2,5-bis-trimethylstannylthieno[3,2-b]thiophene (93 mg, 0.2 mmol), Pd$_2$(dba)$_3$ (4 mg, 0.004 mmol, 4 mol % Pd), P(o-tol)$_3$ (3 mg, 0.010 mmol, 5 mol %), LiCl (9 mg, 0.2 mmol) and chlorobenzene (5 ml). The glass vial is purged with nitrogen and securely sealed. The glass vial is placed into a microwave reactor (Emrys Creator, Personal Chemistry Ltd) and heated to 200° C. for 10 minutes. After cooling to RT, the reaction mixture is precipitated into a mixture of acetone (50 mL) and 37% hydrochloric acid (5 mL), and stirred for 1 h. The polymer is filtered off, washed with acetone, and dried under vacuum. The polymer is washed (via Soxhlet extraction) with acetone for 18 h and petroleum ether 40-60 for 6 h, and dried under vacuum to afford the product as a red solid (98 mg, 80%). GPC(CHCl$_3$) Mn (5,400 g/mol), Mw (6,800 g/mol). $\lambda_{max}$ 463 nm (solid film). $^1$H NMR as expected.

Example 10

Polymer 15 is prepared as described below:

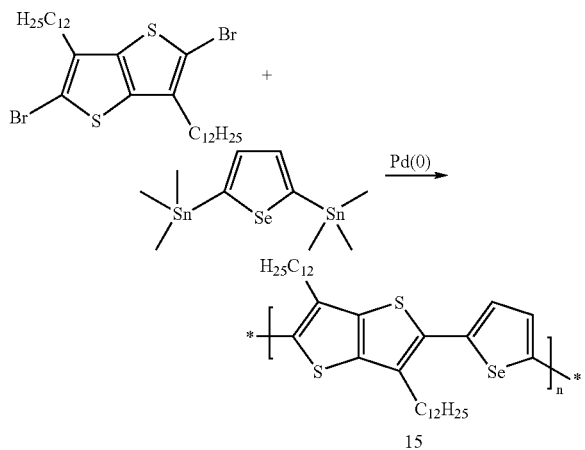

Poly(3,6-didodecylthieno[3,2-b]thiophene-co-selenophene) (15)

A 10 ml glass vial is charged with a stirrer bar, 2,5-dibromo-3,6-didodecylthieno[3,2-b]thiophene (127 mg, 0.2 mmol), 2,5-bis-trimethylstannylselenophene (91 mg, 0.2 mmol), Pd$_2$(dba)$_3$ (4 mg, 0.004 mmol, 4 mol % Pd), P(o-tol)$_3$ (5 mg, 0.016 mmol, 8 mol %) and anhydrous THF (4 ml). The glass vial is purged with nitrogen and securely sealed. The glass vial is placed into a microwave reactor (Emrys Creator, Personal Chemistry Ltd) and heated to 150° C. for 10 minutes. After cooling to RT, the reaction mixture is precipitated into a mixture of methanol (50 mL) and 37% hydrochloric acid (5 mL), and stirred for 1 h. The polymer is filtered off, washed with methanol, and dried under vacuum. The polymer is washed (via Soxhlet extraction) with acetone for 8 h and petroleum ether 40-60 for 8 h, and dried under vacuum to afford the product as a dark red solid. GPC(CHCl$_3$) Mn (6,300 g/mol), Mw (9,300 g/mol). $\lambda_{max}$ 572 nm (solid film). $^1$H NMR as expected.

Example 11

Transistor Fabrication and Measurement

Thin-film organic field-effect transistors (OFETs) are fabricated on highly doped silicon substrates with thermally grown silicon oxide (SiO$_2$) insulating layer, where the substrate served as a common gate electrode. Transistor source-drain gold electrodes are photolithographically defined on the SiO$_2$ layer. Prior to organic semiconductor deposition, FET substrates are treated with a silylating agent hexamethyldisilazane (HMDS). Thin semiconductor films are then deposited by spin-coating polymer solutions in chloroform, xylene, chlorobenzene or dichlorobenzene (0.4-1.0 wt %) on FET substrates. The electrical characterization of the transistor devices, is carried out under ambient atmosphere using computer controlled Agilent 4155C Semiconductor Parameter Analyser.

Transistor characteristics for examples 1-3 (compounds 3, 7 and 8) and examples 5-10 (compounds 10-15) are measured on films prepared by spin coating (Table 1). The films are heated to 100° C. for 10 min under nitrogen to remove residual solvent, and then cooled to room temperature to measure the transistor characteristics. The transfer and output characteristics for example 2 (compound 7) are shown FIG. 1. The devices showed typical p-type behaviour with good current modulation, and well-defined linear and saturation regimes. Field effect mobility is calculated in the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \tag{1}$$

where W is the channel width, L the channel length, $C_i$ the capacitance of insulating layer, $V_g$ the gate voltage, $V_d$ the drain voltage, $I_d$ is the drain current, $V_0$ the turn-on voltage and $\mu^{sat}$ is the saturated charge carrier mobility. Turn-on voltage ($V_0$) is determined as the onset of source-drain current (FIG. 1).

TABLE 1

| Material | Transistor Characteristics | |
| --- | --- | --- |
| | Saturated Mobility ($\mu^{sat}$) | On/off ratio |
| 3 | 1.0 × 10$^{-6}$ cm$^2$/Vs | 1 × 10$^4$ |
| 7 | 8.8 × 10$^{-2}$ cm$^2$/Vs | 1 × 10$^6$ |
| 8 | 1.7 × 10$^{-5}$ cm$^2$/Vs | 1 × 10$^4$ |
| 10 | 4.3 × 10$^{-3}$ cm$^2$/Vs | 1 × 10$^4$ |
| 11 | 2.0 × 10$^{-3}$ cm$^2$/Vs | 1 × 10$^4$ |
| 12 | 5.2 × 10$^{-2}$ cm$^2$/Vs | 3 × 10$^5$ |
| 13 | 4.2 × 10$^{-2}$ cm$^2$/Vs | 1 × 10$^7$ |
| 14 | 1.0 × 10$^{-3}$ cm$^2$/Vs | 1 × 10$^4$ |
| 15 | 6.5 × 10$^{-2}$ cm$^2$/Vs | 1 × 10$^6$ |

The invention claimed is:

1. A monomer, oligomer, or polymer compound comprising a structure according to formula I ([A]$_a$[B]$_b$[C]$_c$[D]$_d$)$_n$-       I wherein A and C are each, independently of one another,

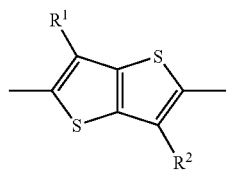

B and D are each, independently of one another, —CX$^1$═CX$^2$—, or —C≡C—, or an arylene or heteroarylene group that is optionally substituted with one or more groups R$^1$, R[1] and R[2] are each, independently of one another, H or halogen, or an aryl or heteroaryl group which is optionally substituted, or a straight chain, branched or cyclic alkyl with 1 to 20 C-atoms and which is unsubstituted or mono- or polysubstituted by F, Cl, Br, I or CN, and wherein optionally one or more non-adjacent $CH_2$ groups are replaced, in each case independently from one another, by —O—, —S—, —NH—, —NR$^0$—, —SiR$^0$R$^{00}$—, —CO—, —COO—, —OCO—, —O—CO—O—, —S—CO—, —CO—S—, —CX$^1$=CX$^2$— or —C≡C— in such a manner that O and/or S atoms are not linked directly to one another, X[1] and X[2] are each, independently of one another, H, F, Cl or CN, R$^0$ and R$^{00}$ are each, independently of one another, H, alkyl with 1 to 12 C-atoms, or aryl, a and c are each, independently of one another, 0 or 1, wherein in at least one group [(A)$_a$-(B)$_b$-(C)$_c$(D)$_d$] a and/or c is 1, b and d are each, independently of one another, 0, 1 or 2, and n is an integer from 1 to 10,000, wherein in case n>1 the groups [(A)$_a$-(B)$_b$-(C)$_c$-(D)$_d$] can be identical or different, and with the provisos that:

a) said compound comprise at least one group A or C that is substituted by groups R[1] and R[2] each having at least 3 C-atoms, and/or b) said compound comprise at least one group B or D that is thiophene-2,5-diyl or selenophene-2,5-diyl substituted in 3- and/or 4-position by a group R[1] being different from H;

and with the proviso that said compound does not contain a thieno[2,3-b]thiophene group.

2. A monomer, oligomer, or polymer compound according to claim 1, wherein said compound is a compound of formula I1

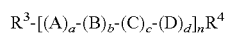

wherein

R[3] and R[4] are each, independently, H, $C_1$-$C_{12}$-alkyl, halogen, Sn(R$^0$)$_3$, B(OR$^0$)$_2$, $CH_2Cl$, COH, CH=$CH_2$, or SiR$^0$R$^{00}$R$^{000}$, or an optionally substituted aryl or heteroaryl group, R$^{000}$ is H, alkyl with 1 to 12 C-atoms, or aryl.

3. An oligomer or polymer compound according to claim 1, wherein said compound has a degree of polymerization (n) from 10 to 5000.

4. A monomer, oligomer, or polymer compound according to claim 1, wherein R[1] and R[2] are selected from $C_3$-$C_{20}$-alkyl that is optionally substituted with one or more fluorine atoms, $C_3$-$C_{20}$-alkenyl, $C_3$-$C_{20}$-alkynyl, $C_3$-$C_{20}$-ester, $C_3$-$C_{20}$-amino, $C_3$-$C_{20}$-fluoroalkyl, an 4 optionally substituted aryl, and optionally substituted heteroaryl.

5. A monomer, oligomer, or polymer compound according claim 1, wherein B and D are selected from:

1,4-phenylene, fluorinated 1,4-phenylene, 2,5-pyridine, 2,5-pyrimidine, p,p'-biphenyl, naphthalene-2,6-diyl, thiophene-2,5-diyl, selenophene-2,5-diyl, fluorinated or alkylated thiophene-2,5-diyl or selenophene-2,5-diyl, 2,2-dithiophene, fluorinated or alkylated 2,2-dithiophene, fluorinated benzo[1,2-b:4,5-b'] dithiophene, 2,5-thiazole, 2,5-thiadiazole, 2,5-oxazole and 2,5-oxadiazole, which in each case is unsubstituted or mono- or polysubstituted with L, wherein L is F, Cl, Br, or an alkyl, alkoxy, alkylcarbonyl or alkoxycarbonyl group having up to 12 C atoms and wherein one or more H atoms are each optionally replaced by F or Cl.

6. A monomer, oligomer, or polymer compound according to claim 1, wherein -([A]$_a$-[B]$_b$-[C]$_c$-[D]$_d$)$_n$- is selected from the following formulae

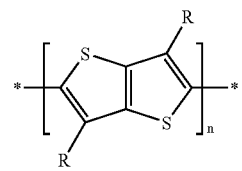

Ia

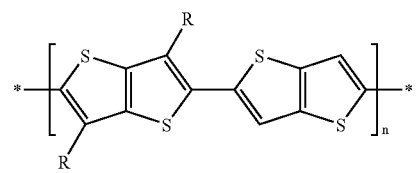

Ib

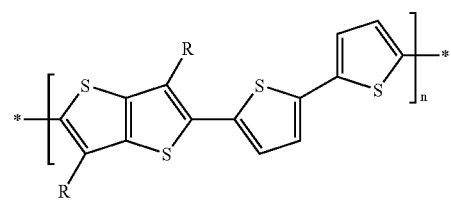

Ic

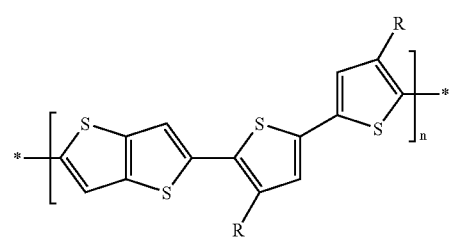

Id

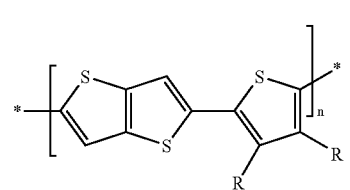

Ie

If

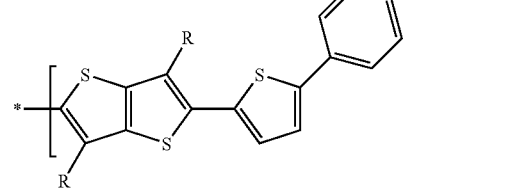

Ig

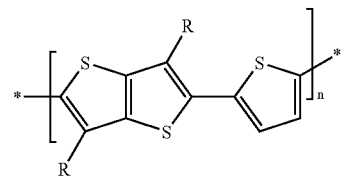

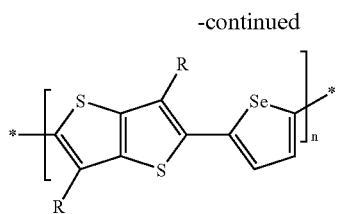

wherein R is H or halogen, or an aryl or heteroaryl group which is optionally substituted, or a straight chain, branched or cyclic alkyl with 1 to 20 C-atoms and which is unsubstituted or mono- or polysubstituted by F, Cl, Br, I or CN and wherein optionally one or more non-adjacent $CH_2$ groups are replaced, in each case independently from one another, by —O—, —S—, —NH—, —NR$^o$—, —SiR$^o$R$^{oo}$—, —CO—, —COO—, —OCO—, —O—CO—O—, —S—CO—, —CO—S—, —CX$^1$═CX$^2$— or —C≡C— in such a manner that O and/or S atoms are not linked directly to one another.

7. In an optical, electrooptical or electronic components or devices, organic field effect transistors (OFET), integrated circuitry (IC), thin film transistors (TFT), flat panel displays, radio frequency identification (RFID) tags, electroluminescent or photoluminescent devices or components, organic light emitting diodes (OLED), backlights of displays, photovoltaic or sensor devices, charge injection layers, Schottky diodes, planarizing-layers, antistatic films, conducting substrates or patterns, electrode materials in batteries, photoconductors, electrophotographic applications, electrophotographic recording, organic memory devices, alignment layers, cosmetic or pharmaceutical compositions, comprising a charge-transport, semiconducting, electrically conducting, photoconducting or light-emitting material, the improvement wherein said material comprises a monomer, oligomer, or polymer compound according to claim 1.

8. An optical, electrooptical or electronic device, FET, integrated circuit (IC), TFT, OLED or alignment layer comprising a material according to claim 1.

9. A TFT or TFT away for flat panel displays, radio frequency identification (RFID) tag, electroluminescent display or backlight, comprising a material comprising a monomer, oligomer, or polymer according to claim 1.

10. A security marking or device comprising a FET according to claim 8.

11. A monomer, oligomer, or polymer compound according to claim 1, wherein said compound is oxidatively or reductively doped to form a conducting ionic species.

12. A charge injection layer, planarizing layer, antistatic film or conducting substrate or pattern for electronic applications or flat panel displays, comprising a monomer, oligomer, or polymer compound according to claim 11.

13. A monomer, oligomer, or polymer compound according to claim 1, wherein optionally substituted aryl or heteroaryl groups for R$^1$ and R$^2$ are selected from mono-, bi- or tricyclic aromatic or heteroaromatic groups with up to 25 C atoms, wherein the rings can be fused, and in which the heteroaromatic group contains at least one hetero ring atom selected from N, O and S, wherein said aromatic or heteroaromatic groups are unsubstituted of substituted with one or more of F, Cl, Br, I, CN, and straight chain, branched or cyclic alkyl having 1 to 20 C atoms which is unsubstituted or mono- or poly-substituted by F, Cl, Br, I, —CN or —OH, and in which one or more non-adjacent $CH_2$ groups are each optionally replaced, independently, by —O—, —S—, —NH—, —NR$^o$—, —SiR$^o$R$^{oo}$—, —CO—, —COO—, —OCO—, —OCO—O, —S—CO—, —CO—S—, —CH═CH— or —C≡C— in such a manner that O and/or S atoms are not linked directly to one another.

14. A monomer, oligomer, or polymer compound according to claim 1, wherein optionally substituted aryl or heteroaryl groups for R$^1$-R$^4$ are selected from mono-, bi- or tricyclic aromatic or heteroaromatic groups with up to 25 C atoms, wherein the rings can be fused, and in which the heteroaromatic group contains at least one hetero ring atom selected from N, O and S, wherein said aromatic or heteroaromatic groups are unsubstituted of substituted with one or more of F, Cl, Br, I, CN, and straight chain, branched or cyclic alkyl having 1 to 20 C atoms which is unsubstituted or mono- or poly-substituted by F, Cl, Br, I, —CN or —OH, and in which one or more non-adjacent $CH_2$ groups are each optionally replaced, independently, by —O—, —S—, —NH—, —NR$^o$—, —SiR$^o$R$^{oo}$—, —CO—, —COO—, —OCO—, —OCO—O, —S—CO—, —CO—S—, —CH═CH— or —C≡C— in such a manner that O and/or S atoms are not linked directly to one another.

15. An oligomer or polymer compound according to claim 1, wherein said compound has identical recurring units $[(A)_a\text{-}(B)_b\text{-}(C)_c\text{-}(D)_d]$.

16. A monomer, oligomer, or polymer compound according to claim 1, wherein R$^1$ and R$^2$ are identical groups.

17. An oligomer or polymer compound according to claim 3, wherein said compound has a degree of polymerization (n) from 20 to 1000.

18. An oligomer or polymer compound according to claim 1, wherein said compound has a molecular weight from 5000 to 300,000.

19. An oligomer or polymer compound according to claim 18, wherein said compound has a molecular weight from 10,000 to 100,000.

20. A polymer compound according to claim 1, wherein the monomeric units of said polymer consist of identical recurring units of the formulae $(A\text{-}B)_n$, $(A\text{-}B\text{-}C)_n$, $(A\text{-}B\text{-}D)_n$, $(A\text{-}C\text{-}D)_n$, $(B\text{-}C\text{-}D)_n$ or $(A\text{-}B\text{-}C\text{-}D)_n$.

21. A monomer, oligomer, or polymer compound according to claim 1, wherein b is 1 and B is thiophene-2,5-diyl or selenophene-2,5-diyl that is optionally substituted by one or two groups R$^1$ that are different from H.

22. A monomer, oligomer, or polymer compound according to claim 2, wherein R$^3$ and R$^4$ are selected from H, $C_1$-$C_{12}$-alkyl, halogen, Sn(R$^o$)$_3$, B(OR$^o$)$_2$CH$_2$Cl, CH$_2$OH, CH═CH$_2$, SiR$^o$R$^{oo}$R$^{ooo}$, optionally substituted aryl, and optionally substituted heteroaryl.

23. A polymer compound according to claim 1, wherein said compound is poly(3,6-dioctylthieno[3,2-b]thiophene).

24. A polymer compound according to claim 1, wherein said compound is poly(2,5-bis(3-decylthiophen-2-yl)thieno[3,2-b]thiophene).

25. A polymer compound according to claim 1, wherein said compound is poly(3,4-didecylthiophene-co-thieno[3,2-b]thiophene).

26. A polymer compound according to claim 1, wherein said compound is poly(3,6-dioctylthieno[3,2-b]thiophene-co-thieno[3,2-b]thiophene).

27. A polymer compound according to claim 1, wherein said compound is poly(3,6-dioctylthieno[3,2-b]thiophene-co-thiophene).

28. A polymer compound according to claim 1, wherein said compound is poly(3,6-dioctylthieno[3,2-b]thiophene-co-bithiophene).

29. A polymer compound according to claim 1, wherein said compound is poly(3,6-didodecylthieno[3,2-b]thiophene-co-thiophene); poly(3,6-didodecylthieno[3,2-b]thiophene-co-bithiophene); poly(3,6-didodecylthieno[3,2-b]thiophene-co-thieno[3,2-b]thiophene); or poly(3,6-didodecylthieno[3,2-b]thiophene-co-selenophene).

* * * * *